United States Patent [19]

Cerami

[11] Patent Number: 4,761,368
[45] Date of Patent: Aug. 2, 1988

[54] METHOD AND AGENTS FOR MEASURING PROTEIN AGING

[75] Inventor: Anthony Cerami, Flanders, N.J.

[73] Assignee: The Rockefeller University, New York, N.Y.

[21] Appl. No.: 885,967

[22] Filed: Jul. 15, 1986

[51] Int. Cl.$^4$ .................... G01N 53/00; G01N 33/48; C07K 15/00

[52] U.S. Cl. ........................ 435/7; 435/810; 436/63; 436/518; 436/536; 436/538; 436/542; 436/544; 436/815; 530/370; 530/380; 530/387; 530/395; 530/807

[58] Field of Search ............ 435/7, 288, 810; 436/63, 518, 536, 538, 542, 544, 815; 530/370, 380, 387, 395, 807

[56] References Cited

U.S. PATENT DOCUMENTS 4,440,863  4/1984  Haagensen, Jr. ................ 436/539
4,665,192  5/1987  Cerami ........................ 548/336

OTHER PUBLICATIONS

Maillard, L. C. (1912) C. R. Acad. Sci (Paris) 154, 66–68.
Bunn, H. F., Haney, D. N., Ga-bay, K. H. & Gallop, P. H. (1975) Biochem. Biophys. Res. Commun. 67, 103–109.
Monnier, V. M. & Cerami, A. (1983) in Maillard Reaction in Food and Nutrition, ed. Waller, G. A. (American Chemical Society, Washington, D.C.), vol. 215, pp. 431–449.
Koenig., R. J., Blobstein, S. H. & Cerami, A. (1977) J. Biol. Chem. 252, 2992–2997.
Monnier, V. M. & Cerami, A. (1983) Biochem. Biophys. Acta 760, 97–103.
Monnier, V. M., Kohn, R. R. & Cerami, A. (1984) Proc. Natl. Acad. Sci., U.S.A. 81, 583–587.
Brownlee, M., Pongor, S. & Cerami, A. (1983) J. Exp. Med. 158, 1739–1744.
Monnier, V. M. & Cerami, A. (1981) Science 211, 491–493.
Pongor, S., Kramer, J. & Ungar, E. (1980) J. High Resolut. Chromatogr. Chromatogr. Commun. 3, 93–94.
Chait, B. T., Agosta, W. C. & Field, F. H. (1981) Int. J. Mass Spectrom Ion Phys. 39, 339–366.
Silverstein, R. M. & Bassler, G. C. (1967) Spectrometric Identification Organic Compounds (Wiley, N.Y.), 2nd Ed., pp. 144–145.
Schubert, W., Hellwig, A. & Bleichert, J. L. (1964) J. Prakt. Chem. 24, 125–131.
Bucala, R., Model, P. & Cerami, A. (1983) Proc. Natl. Acad. Sci. U.S.A. 81, 105–109.
Pongor, S., Ulrich, P. C., Bencsath, A., and Cerami, A. (1984) Proc. Natl. Acad. Sci. U.S.A. 81, pp. 2684–2688.

Primary Examiner—Sidney Marantz
Assistant Examiner—Richard Wagner
Attorney, Agent, or Firm—Klauber & Jackson

[57] ABSTRACT

A new and useful fluorescent chromophore has been isolated and identified which has been observed in proteins exposed to glucose over time, and whose fluorescent properties closely resemble those of the polypeptide after it undergoes advanced glycosylation. The chromophore has been structurally identified and named 2-furoyl-4(5)-(2-furanyl)-1$\underline{H}$-imidazole, and is believed to be one of the end products of extended nonenzymatic polypeptide glycosylation, which results in the state known as nonenzymatic browning (NEB). The measurement of this chromophore makes possible both qualitative and quantitative assessment of the degree of aging. Diagnostic and test kits are also disclosed.

11 Claims, 6 Drawing Sheets

METHOD AND AGENTS FOR MEASURING PROTEIN AGING

This is a division of application Ser. No. 590,820, filed Mar. 19, 1984, now U.S. Pat. No. 4,665,192, issued May 12, 1987.

This invention was made with partial assistance from grants from the National Institutes of Health and the Brookdale Foundation.

RELATED PUBLICATIONS

The Applicant is a co-author of the following article directed to the subject matter of the present invention: "AGING OF PROTEINS: ISOLATION AND IDENTIFICATION OF A FLUORESCENT CHROMOPHORE FROM THE REACTION OF POLYPEPTIDES WITH GLUCOSE"; Sandor Pongor, Peter C. Ulrich, A. Aladar Bencsath and Anthony Cerami, (May, 1984) Proc. Natl. Acad. Sci. U.S.A., Vol. 81, pp. 2684-2688 incorporated herein by reference.

BACKGROUND OF THE INVENTION

1. Field of the Invention

The present invention is directed generally to the reaction that occurs between glucose and proteins, and more specifically to the study of the effects of this reaction upon the structure and activity of the glycosylated polypeptide.

2. Description of the Prior Art

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Maillard, L. C. (1912) C.R. Acad. Sci., Vol. 154, pp. 66-68.

In the years that followed the initial discovery by Maillard, food chemists studied the hypothesized reaction in detail and determined that stored and heat treated foods undergo nonenzymatic browning as a result of the reaction between glucose and the polypeptide chain, and that the proteins are resultingly crosslinked and correspondingly exhibit decreased bioavailability. Finot, P. A. (1982) in *Modification of Proteins*, eds, Feeney, R. E. and Whitaker, J. R., American Chemical Society, Vol. 198, pp. 91-124, Washington, D.C. At this point, it was determined that the pigments responsible for the development of the brown color that develops as a result of protein glycosylation possessed characteristic spectra and fluorescent properties, however the chemical structure of the pigments had not been specifically elucidated.

The reaction between reducing sugars and food proteins discussed above was found in recent years to have its parallel in vivo. Thus, the nonenzymatic reaction between glucose and the free amino groups on proteins to form a stable amino 1-deoxy ketosyl adduct, known as the Amadori product, has been shown to occur with hemoglobin, wherein a rearrangement of the amino terminal of the $\beta$-chain of hemoglobin by reaction with glucose, forms the adduct known as hemoglobin $A_{1c}$. This reaction as also found to occur with a variety of other body proteins, such as lens crystallins, collagen and nerve proteins. See, Bunn, H. F., Haney, D. N., Gabbay, K. H. and Gallop, P. H. (1975) Biochem. Biophys. Res. Comm. Vol. 67, pp. 103-109; Koenig, R. J., Blobstein, S. H. and Cerami, A. (1977) J. Biol. Chem. Vol. 252, pp. 2992-2997; Monnier, V. M. and Cerami, A. (1983) in *Maillard Reaction in Food and Nutrition*, ed. Waller, G. A., American Chemical Society, Vol. 215, pp. 431-448; and Monnier, V. M. and Cerami, A., (1982) Clinics in Endochrinology and Metabolism Vol. 11, pp. 431-452. Moreover, brown pigments with spectral and fluorescent properties similar to those of late-stage Maillard products have also been observed in vivo in association with several long-lived proteins, such as lens proteins and collagen from aged individuals. An age related linear increase in pigment was observed in human dura collagen between the ages of 20 to 90 years. See, Monnier, V. M. and Cerami, A. (1983) Biochem. Biophys. Acta, Vol. 760, pp. 97-103; and, Monnier, V. M., Kohn, R. R. and Cerami, A. "Accelerated Age-Related Browning of Human Collagen in Diabetes Mellitus", Proc. Nat. Acad. Sci. U.S.A., Vol. 81, pp. 583-587 (January 1984). Interestingly, the aging of collagen can be mimicked in vitro by the crosslinking induced by glucose; and the capture of other proteins and the formation of adducts by collagen, also noted, is theorized to occur by a crosslinking reaction, and is believed to account for the observed accumulation of albumin and antibodies in kidney basement membrane. See, Brownlee, M., Pongor, S. and Cerami, A. (1983) J. Exp. Med., Vol. 158, pp. 1739-1744.

In general, little detailed information is available on the chemistry of the late-stage Maillard process, and it has been correspondingly difficult to determine the relation if any, that nonenzymatic browning may bear to the structural and functional changes in tissues that occur during the aging process, and has likewise been observed to occur at an accelerated rate in individuals suffering from diabetes mellitus. Accordingly, a need therefore exists to identify to the extent possible, the structure and activity of the end products of advanced protein glycosylation, to aid in identifying the occurrence of advanced glycosylation, and to serve as an exploratory tool for the development and test of possible agents and corresponding treatments designed to retard or inhibit this form of protein aging.

SUMMARY OF THE INVENTION

In accordance with the present invention, a fluorescent chromophore has been isolated and identified, which is found to be present in certain browned polypeptides such as bovine serum albumin and poly-L-lysine. The compound has been assigned the novel structure 2-(2-furoyl)-4(5)-2(furanyl)-1H-imidazole. The compound was isolated by the hydrolysis of the browned polypeptides followed by alkalinization, extraction into organic solvents and subsequent purification by silica gel chromotography.

Correspondingly, the present invention relates to the synthesis of this novel chromophore, by the nonenzymatic reaction of the named proteins with glucose to the late-stage formation of the brown pigment, followed by acid hydrolysis, alkalinization, extraction into organic solvents and final purification. Alternately, the compound may be synthesized by the reaction of furylglyoxal and ammonia.

The novel compound of the present invention exists in a tautomeric state due to the incorporation in its structure of two peptide-derived amine nitrogens. The incorporation of these amine nitrogens and two glucose residues in the novel compound suggests that its peptide-bound precursor may be implicated in the in vivo crosslinking of proteins by glucose, which is observed in the late stage of the Maillard process.

The present invention also relates to a method for measuring the presence of advanced glycosylation end products in browned proteins, by measuring the activity and presence of the novel compound of the present invention. More particularly, the activity of the novel compound may be followed directly by the assay techniques discussed later on, through the use of an appropriately labeled quantity of the compound. Alternately, the compound can be used to raise binding partners or antibodies that could in turn, be labeled and introduced into a medium containing a browned protein under investigation to compete for the unlabeled chromophore present in the protein sample.

Thus, both the fluorescent chromophore of present invention and any antibodies that may be raised therefrom, are capable of use in connection with various diagnostic techniques, including immunoassays, such as a radioimmunoassay, using for example, a chromophore labeled by either radioactive addition, reduction with sodium borohydride, or radioiodination.

In an immunoassay a control quantity of the chromophore its antibody, or the like may be prepared and labeled with an enzyme, a specific binding partner and/or a radioactive element, and may then be introduced into a sample of protein material believed to be in the process of undergoing glycosylation. After the labeled chromophore or its binding partner(s) has had an opportunity to react with available protein material, the resulting mass may be examined by known detecting techniques, which may vary with the nature of the label attached.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized colorimetric, spectrophotometric, fluorospectrophotometric or gasometric techniques known in the art.

The present invention includes an assay system which may be prepared in the form of a test kit for the quantitative analysis of the extent of nonenzymatic protein glycosylation. The system or test kit may comprise a labeled component prepared by one of the radioactive and/or enzymatic techniques discussed herein, coupling a component of one of the advanced glycosylation end products, such as the present fluorescent chromophore; and one or more additional immunochemical reagents, at least one of which is a free or immobilized ligand, capable either of binding with the labeled component, its binding partner, one of the components to be determined or their binding partner(s).

In conjunction with the investigative methods and materials identified herein, the invention may extend to potential methods of treatment to either retard or inhibit the glycosylation of proteins, by a procedure involving the examination of the protein sample for the presence of the fluorescent chromophore 2-(2-furoyl)-4(5)-(2-furanyl)-1H-imidazole, in accordance with one of the methods specified earlier; followed by the development of a first binding partner or antibody to the chromophore, the subsequent development of a second binding partner or antibody specific to the first binding partner, and the administration of the latter binding partner either to the remainder of the protein mass in the instance of foodstuffs, or the area from which the protein sample was taken in the instance of living animal tissue or serum, in an effort to prevent the protein mass from entering the final stage of the Maillard process.

The identification of the fluorescent chromophore of the present invention makes possible the continued investigation of the Maillard process and promotes efforts to identify other specific end products of advanced protein glycosylation. The chromophore and the various investigative methods associated with its isolation and identification will assist in elucidating the details of the chemical reactions that constitute late stage glycosylation, and will hopefully hold the key to identifying specific agents that can serve to retard or inhibit the Maillard process and thereby extend the useful life of the protein. This development is particularly important as the proteins most acutely affected by the Maillard process, such as collagen, are present in substantial quantities in many of the important body tissues, and correspondingly exert a pronounced effect on the functioning of the body with the onset of advanced age.

An additional application of the present invention is to the science of food technology, as the fluorescent chromophore and the assay procedures in which it is useful, may be employed to test for and identify undesirable and possibly toxic deterioration of foodstuffs. Thus, various foodstuffs could be periodically inspected by resorting to one of the assay procedures set forth above, to determine with quantitative exactitude, the onset and extent of protein aging. Such accuracy is particularly possible in the instance where the present fluorescent chromophore is incorporated into a radioimmunoassay system, such as one employing radioiodination or the introduction of a radioactive label by reduction of the chromophore with sodium borohydride.

Accordingly, it is a principal object of the present invention to identify a specific fluorescent chromophore present in protein undergoing advanced nonenzymatic glycosylation.

It is a further object of the present invention to provide procedures for the isolation and identification of the fluorescent chromophore as aforesaid on both an in vivo and in vitro basis.

It is a still further object of the present invention to provide methods for measurement of the fluorescent chromophore as aforesaid which served to elucidate the stage of glycosylation of the protein sample under investigation.

It is a still further object of the present invention to provide methods for identifying other advanced glycosylation end products in protein samples subjected to late-stage glycosylation, by assay procedures utilizing the fluorescent chromophore identified herein.

Other objects and advantages will become apparent to those skilled in the art from a review of the ensuing description which proceeds with reference to the following illustrative drawings.

Curve 1 represents poly(L-lysine); curve 2 represents bovine serum albumin; curve 3 represents B-albumin; curve 4 represents B-polylysine; and curve 5 represents FFI isolated from B-polylysine.

Figure 2B:
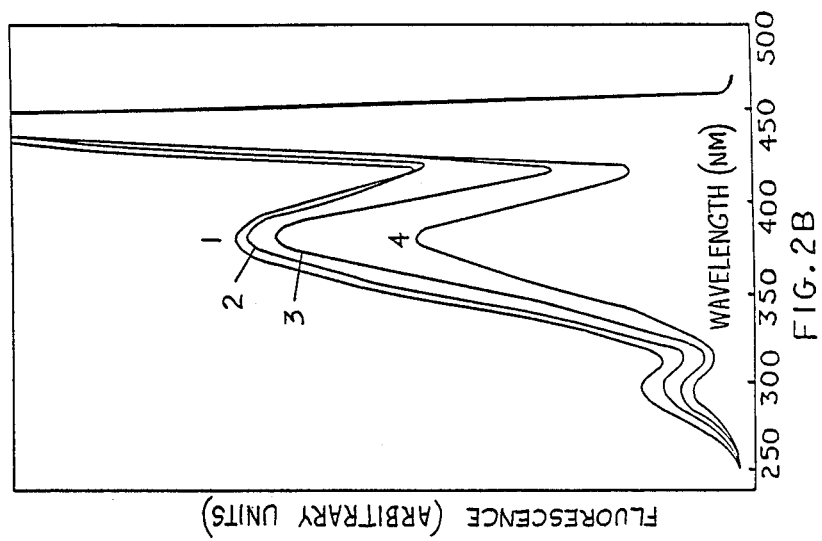
FIG. 2A is a graph depicting the absorbance spectra of the nonenzymatically browned polypeptides, together with control spectra of the polypeptides and the spectrum of the isolated chromophore.

FIG. 2B is a fluorescent excitation spectrum recorded at 440 nm emission, of brown poly-L-lysine and bovine serum albumin, together with the fluorescent chromophore isolates of each.

Curve 1 represents B-polylysine; curve 2 represents B-albumin; curve 3 represents FFI isolated from B-polylysine; and curve 4 represents FFI isolated from B-albumin.

Figure 3:
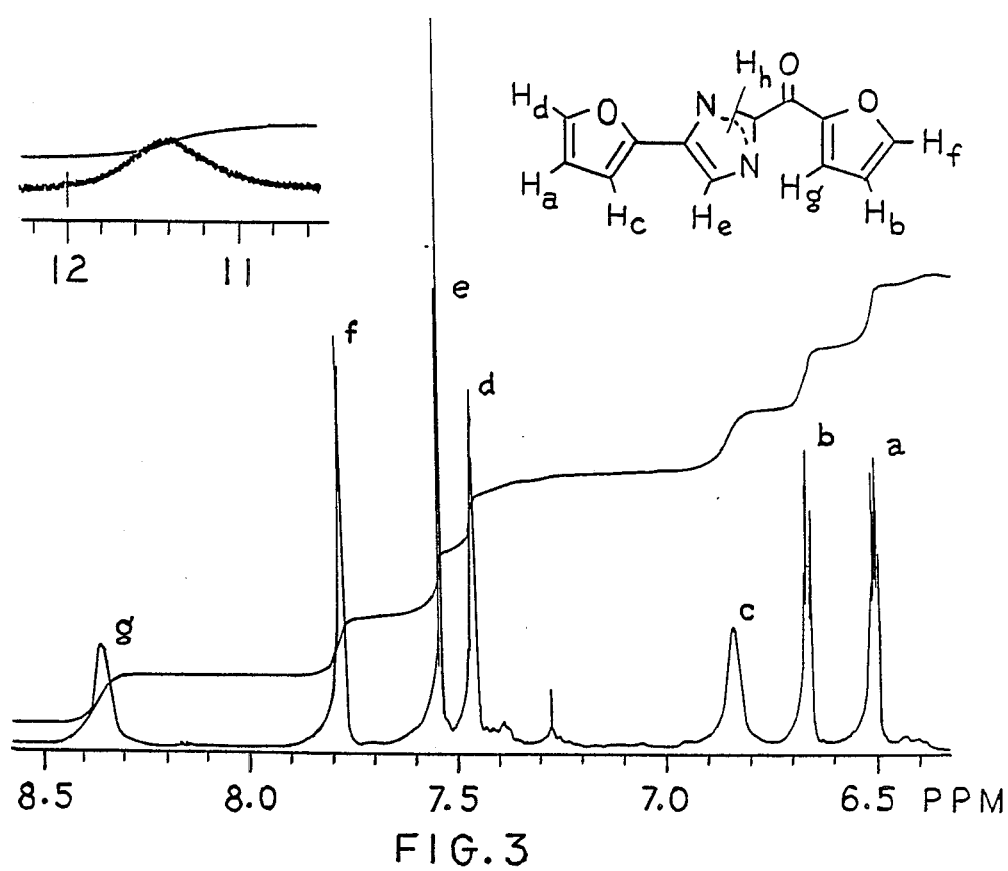

FIG. 3 is a reproduction of the nuclear magnetic resonance spectrum of the fluorescent chromophore of the invention isolated from browned poly-L-lysine ($CDCl_3$, 300 MHZ, with $^1H$-NMR).

Figure 4:

FIG. 4 is a representation of the tautomeric chemical structure postulated to represent the fluorescent chromophore isolated in accordance with the present invention.

Figure 5A:
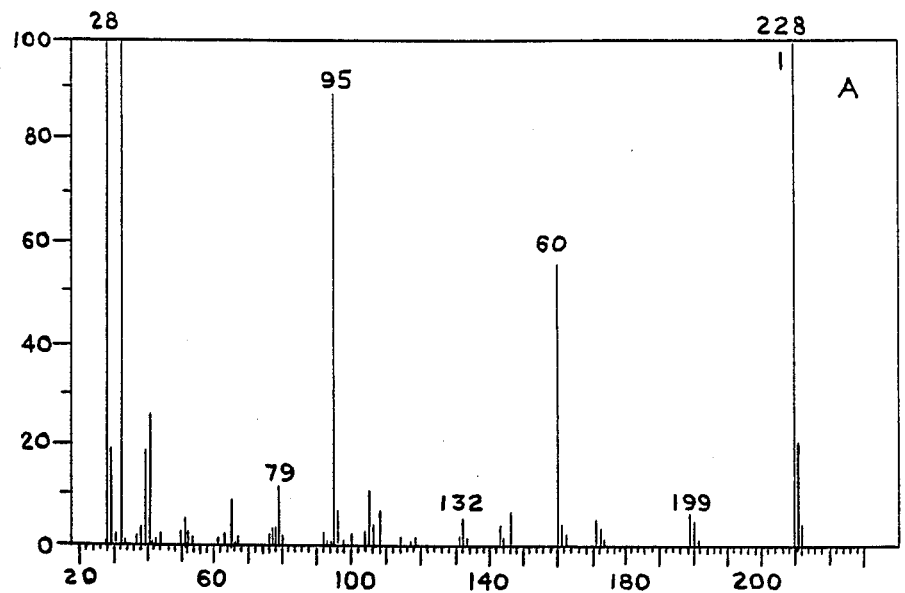
Figure 5B:
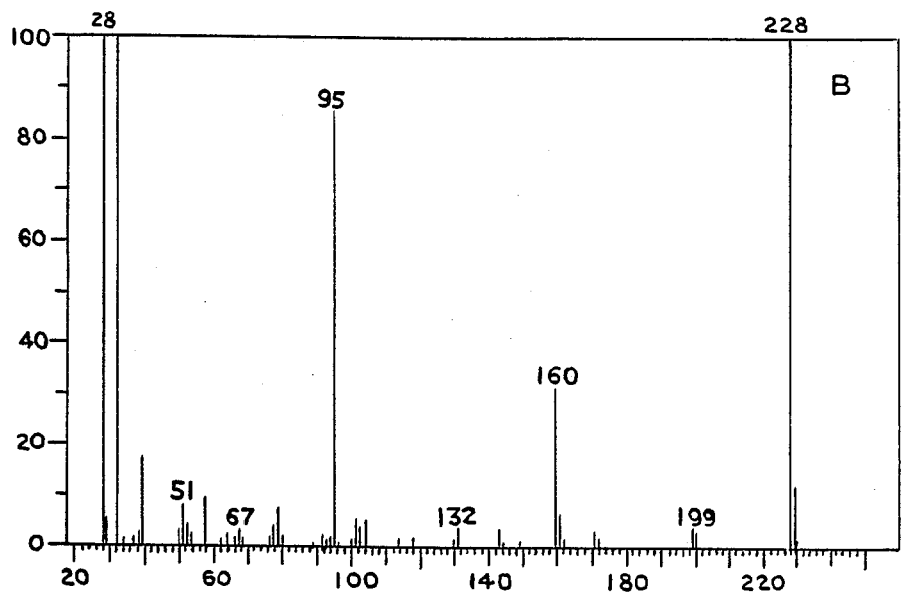
Figure 5C:
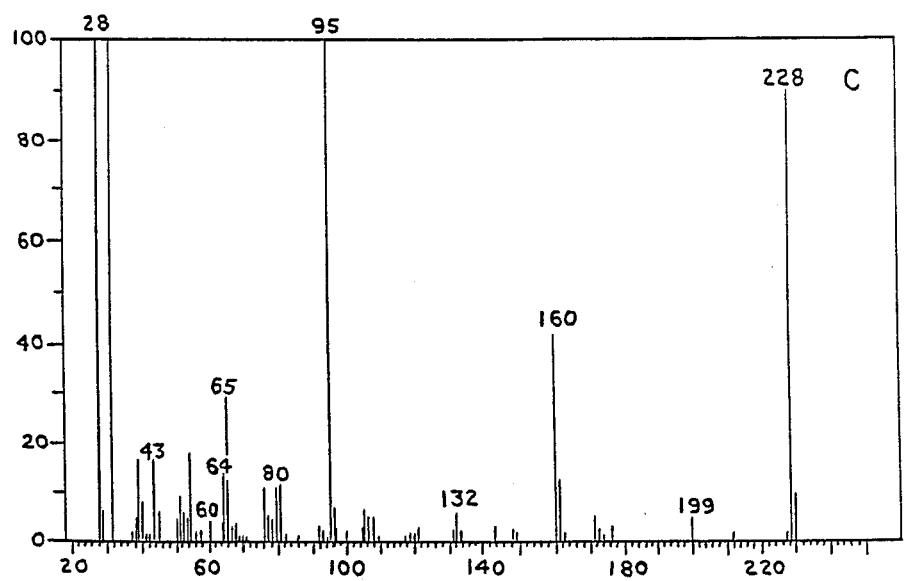

FIGS. 5A–5C comprise electron impact ionization mass spectra of the fluorescent chromophore of the present invention as obtained by in vitro chemical synthesis (FIG. 5A); as isolated from brown poly-L-lysine (FIG. 5B); and as isolated from brown bovine serum albumin (FIG. 5C).

Figure 6:
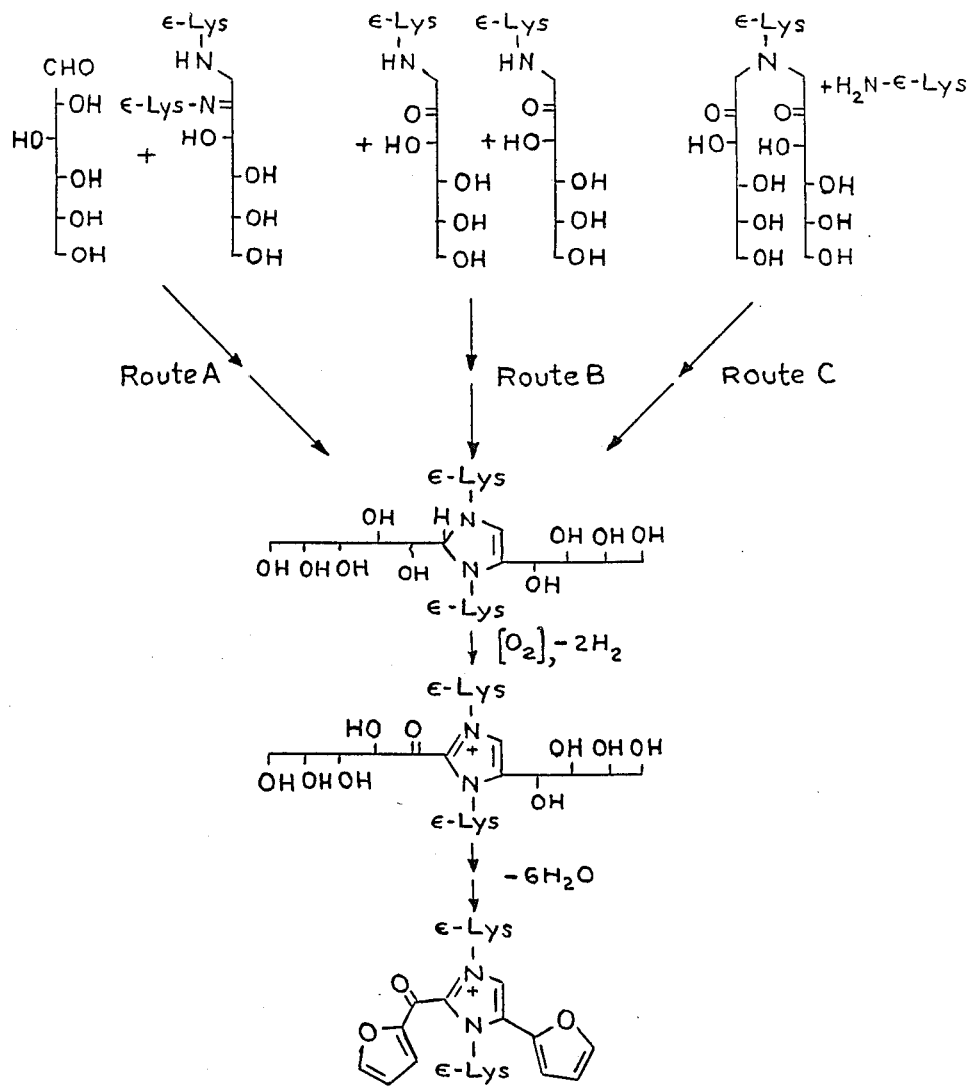

FIG. 6 is a diagram depicting possible reaction pathways between precursor compounds believed to form protein crosslinks similar in structure to the fluorescent chromophore isolated in accordance with the present invention.

DETAILED DESCRIPTION

In its primary aspect, the present invention concerns the isolation and identification of a fluorescent chromophore which has been found to be present in proteins that have been incubated with glucose. In particular, such proteins exhibit several physicochemical changes, including the formation of a brown color, fluorescence and crosslinking. The fluorescent chromophore which has been isolated and identified herein as 2-(2-furoyl)-4(5)-(2-furanyl)-1H-imidazole, appears to represent a cleaved form of a key intermediate in the process initially identified by Maillard and discussed at length hereinabove.

The compound 2-(2-furoyl)-4(5)-(2-furanyl)-1H-imidazole (referred to hereinafter for brevity as FFI) is a condensation product of two glucose molecules and two lysine-derived amino groups into a conjugated system of three aromatic heterocycles. As the data presented later on herein demonstrates, the fluorescence properties of FFI are remarkably similar to those of the non-dialyzable pigments that are bound to albumin and to poly-lysine which have undergone extensive nonenzymatic browning with glucose. This similarity implies that there is close analogy between the structure of FFI and that of the chromophoric centers present in the fluorescent pigments. This analogy forms the basis for the belief by the present inventor that the fluorescent chromophore of the invention can serve as a useful tool in the further investigation and explanation of the chemical transformations that take place in the late-stage Maillard reaction.

The chromophore of the invention can be isolated and prepared by alternate techniques. Thus, and in accordance with the investigative procedures of the present invention, proteins, such as poly-L-lysine and bovine serum albumin, can be nonenzymatically reacted with glucose for a period of time sufficient to reach the onset of the formation of browned protein, and such browned protein may then be subjected first to acid hydrolysis, followed by organic solvent extraction, alkalinization and further extraction, the second extraction to separate the fluorescent component from the remainder of the pigment, and final chromatographic separation.

Alternately, the fluorescent chromophore may be prepared by the reaction of furylglyoxal and ammonia. In such instance, and by example, 2-furylglyoxal hydrate may be disposed in a solution of ethanol and water and may be treated with concentrated aqueous ammonia by dropwise introduction of the latter. Subsequently, the resulting product may be separated between water and an organic solvent such as diethylether-dichloromethane. Thereafter, washing of the organic layer and drying with sodium sulfate may be conducted, and upon filtration, will yield a crude chromophore product which can be subjected to further chromatographic separation and purification in similar fashion to the chromophore recovered from the browned protein starting material.

The fluorescent chromophore of the invention may be used in a variety of investigative methods, in an effort to measure the presence and activity of advanced glycosylation end products. Both quantitative and qualitative determinations may be made, including the preparation of the chromophore with various radioactive or enzymatic labels and the introduction of the thus labeled chromophore into a protein mass to determine its state of glycosylation and chemical activity.

The fluorescent chromophore may be labeled by a variety of techniques, depending upon the nature of the investigative procedure that is to be used. Thus, for example, FFI may be reacted with methoxyamine hydrochloride to form the methoxime derivative, or may be reduced with sodium borohydride. This preparation, illustrated later on herein in the chemical derivatization of FFI for mass spectrometry, can be utilized to place a radioactive label on the reduced form of the chromophore, by the reduction with a radioactive form of sodium borohydride. The resulting reduced derivative can then be employed in appropriate assay procedures.

Other labels commonly employed for such assay procedures may also be associated with the present chromophore and, for example, radioactive labels such as $^{14}C$, $^{131}I$, $^3H$, $^{125}I$ and $^{35}S$ may be appropriately introduced to the chromophore.

Other known labels comprise enzymes and fluorescent materials. Fluorescent materials are preferably considered in the instance where other non-fluorescent advanced glycosylation end products are isolated and are to be labeled for use in assay systems. Similarly, fluorescent labels may be used in the instance where the present chromophore has been employed to raise antibodies to itself, which antibodies are non-fluorescent.

A number of fluorescent materials are known and can be utilized as labels. These include, for example, fluorescein, rhodamine and auramine. A particular labeled conjugate that may be developed in accordance herewith is anti-rabbit antibody prepared in goats and conjugated with fluorescein through an isothiocyanate.

Enzyme labels are likewise useful, and can be detected by any of the presently utilized colorimetric, spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and acid phosphatase. U.S. Pat. Nos. 3,654,090; 3,850,752; and 4,016,043 are referred to by way of example for their disclosure of alternate labeling material and methods.

The fluorescent chromophore may be used to produce antibody(ies) to itself which can be produced and isolated by standard methods including the well known hybridoma techniques. The antibody(ies) can be used in another species as though they were antigen(s) to raise antibody(ies). Both types of antibody(ies) can be used to determine the presence and extent of advanced glycosylation in protein masses, whether in foodstuffs, or in the mammalian body. For convenience, the antibody(ies) to the chromophore will be referred to herein as $Ab_1$ and antibody(ies) raised in another species as $Ab_2$.

The presence of advanced glycosylation in protein masses suspected of undergoing the same can be ascertained by the usual immunological procedures applicable to such determinations. A number of useful procedures are known. Three such procedures which are especially useful utilize either the chromophore labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Ch" stands for chromophore:

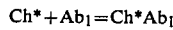

$Ch^* + Ab_1 = Ch^*Ab_1$     A.

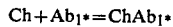

$Ch + Ab_1^* = ChAb_1^*$     B.

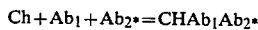

$Ch + Ab_1 + Ab_2^* = CHAb_1Ab_2^*$     C.

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the chromophore substance forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using $Ab_1$ as an antigen. $Ab_2$ therefore would be anti-rabbit antibody raised in goats. For purposes of this description and claims, $Ab_1$ will be referred to as a chromophore antibody and $Ab_2$ will be referred to an an antibody reactive with a chromophore antibody or, in the alternative, an "anti-antibody".

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The chromophore or its binding partner(s) can also be labeled with a radioactive element or with an enzyme. The radioactive label can be detected by any of the currently available counting procedures. The preferred isotope may be selected from $^{14}C$, $^{131}I$, $^{3}H$, $^{125}I$ and $^{35}S$.

In a further embodiment of this invention, commercial test kits suitable for use either by a medical specialist or a food technologist may be prepared to determine the presence or absence of advanced glycosylation end products in a suspected protein sample. In accordance with the testing techniques discussed above, one class of such kits will contain at least the labeled chromophore or its binding partner, an antibody specific thereto. Another which contain at least $Ab_1$ together with labeled $Ab_2$. Still another will contain at least $Ab_1$ and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of late-stage Maillard activity in protein masses, whether in food or in animals, comprising:

(a) a predetermined amount of at least one labeled immunochemically reactive component obtained by the direct or indirect attachment of an advanced glycosylation end product, the present chromophore or a specific binding partner to either, to a detectable label;

(b) other reagents; and (c) directions for use of said kit.

More specifically, the diagnostic test kit may comprise:

(a) a known amount of the chromophore or the advanced glycosylation end product as described above (or a binding partner) generally bound to a solid phase to form a immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling a component of one of said chromophore or said advanced glycosylation end products to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the advanced glycosylation end product and a specific binding partner thereto.

By example, a solid phase assay system or kit may comprise the solid substrate with a quantity of a labeled binding partner for the chromophore FFI immobilized thereon. A supernatant containing the protein to be assayed is then placed in contact with the substrate and a competitive reaction between the labeled material and any unlabeled binding partner(s) in the sample will cause the release of a quantity of the former into the supernatant whereupon it can be precisely quantitatively identified. The foregoing explanation of a particular competitive assay system is presented herein for purposes of illustration only, in fulfillment of the duty to present an enabling disclosure of the invention. It is to be understood that the present invention contemplates a variety of diagnostic protocols within its spirit and scope.

As discussed earlier, the present invention includes potential methods for treating proteins undergoing glycosylation in an effort to retard if not totally inhibit the progress of the Maillard process. The method comprises the development of an anti-antibody to the fluorescent chromophore or to other isolated advanced glycosylation end products, that when administered to the glycosylating protein mass, serves by its structure and reactivity, to block rather than facilitate the continued glycosylation of the protein.

For example, an anti-antibody or second binding partner to a first binding partner to FFI might be raised as in the practice of one of the earlier described assay procedures, which does not cause the proteins to cross-link. In this way, the administration of this non-cross-linking binding partner would block the final insolubilization and hardening of the protein and might thereby prolong its vitality and usefulness, whether in foodstuffs or in animal tissues. The foregoing scenario is naturally illustrative of a course of action that suggests itself as an outgrowth of the findings as to the aging process disclosed presently herein. The invention is not limited to this methodology, but rather encompasses it within its scope. As mentioned earlier, the isolation and identification of the chromophore of the present invention involved the performance of a series of procedures upon representative proteins that were converted in vitro to the browned state. The specific procedures and materials that were used in the preparation of the proteins, and the isolation and analysis of the chromophore that followed, are set forth below in the following illustrative examples.

EXAMPLE I

Preparation and Analyses of the Maillard Products

Poly-L-lysine and bovine serum albumin were chosen as model polypeptides for in vitro glycosylation studies. Accordingly, poly-L-lysine (1 gm; Sigma, St. Louis, MO; Mw 50,000–70,000) was dissolved in 50 ml of sodium phosphate buffer, pH 7.5, 0.5M Na. D-Glucose (50 g) was added an the solution was incubated at 37° C. for 28 days. The solution was dialyzed extensively against distilled water and lyophilized to yield 1.9 g brown polylysine (BPL). Bovine serum albumin (5 g; Sigma, St. Louis, MO) was reacted under analogous conditions to yield 5.2 g of lyophilized brown bovine serim albumin (BBSA).

Figure 1:
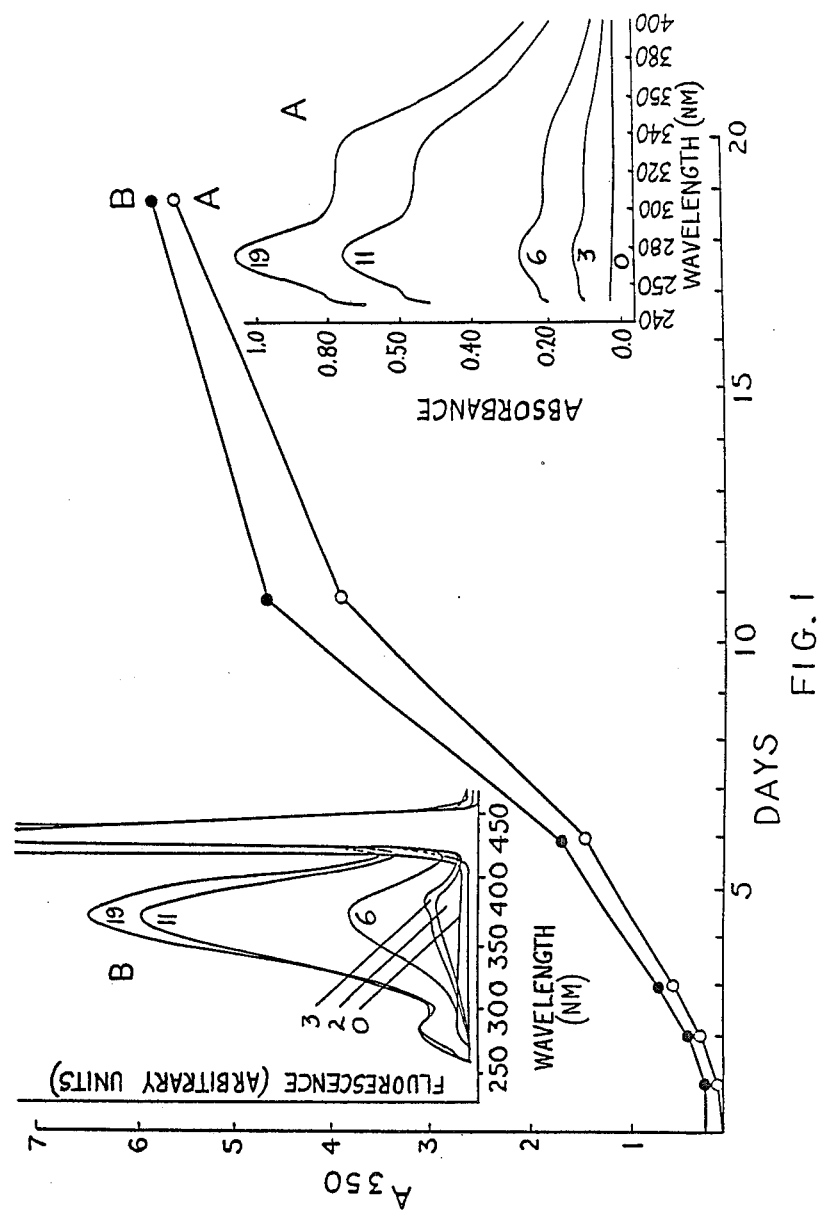
FIG. 1 is a graph depicting the increasing ultraviolet absorbance and fluoresence in the reaction of poly-L-lysine with glucose.

Ultraviolet spectral analysis of the brown polypeptides was conducted and the results are set forth in FIG. 1. The brown poly-L-lysine has a UV absorption maximum at 278 nm, with a prominent shoulder centered around 330–335 nm. The extension of this shoulder into the visible wavelengths is believed to be responsible for the brown color of the material. From the time course shown in FIG. 1, it may be seen that the rate of color formation increased during the first ten days of glucose incubation, and slowed thereafter, probably due to saturation of the available reaction sites.

The excitation fluorescence spectrum of BPL, measured at the emission maximum of 440 nm, shows a major excitation maximum at 370 nm and a minor maximum at 290 nm. These maxima do not correspond with the bands in the UV-visible absorption spectrum. This absence of correlation suggested that the fluorescence was primarily associated with a subclass of Maillard intermediates which might be sufficiently well-defined for chemical isolation and analysis.

EXAMPLE II

Isolation and Analysis of the Fluorescent Product

BPL (1.5 g) was dissolved in 50 ml of 6N HCl. The solution was deoxygenated by perfusion with nitrogen and hydrolyzed for ten hours at 110° C. The hydrolysate was evaporated to dryness in a stream of nitrogen gas at 40° C. and then redissolved in 50 ml of 0.1N HCl. This solution was extracted five times with 50 ml of isobutanol and then five times with 20 ml of chloroform. The organic extracts were discarded. The pH of the aqueous phase was adjusted to 11 with ammonium hydroxide (25%) and the solution was then extracted with 5×20 ml of chloroform. The chloroform extracts were combined and evaporated in a stream of nitrogen (yield: 35 mg). This material was redissolved in 2 ml of chloroform and applied to a 10 mm×200 mm column filled with silica gel (Woelm Co., West Germany), which had been activated at 150° C. overnight and pre-equilibrated with chloroform. The column was washed with 20 ml of chloroform and then the material was eluted with chloroform-methanol (1:1). The yellow fractions were pooled and evaporated to dryness with nitrogen to yield 20 mg of fluorescent compound. BBSA (5 g) was hydrolyzed and worked up under the same conditions described for BPL to yield 2.5 mg of fluorescent compound.

Hydrolysis of BPL yielded predominantly lysine, furosine, and pyridosine, based on ion-exchange TLC comparison with authentic materials; these are known to be the major breakdown products of $\epsilon$-deoxyfructosyl-lysine under acid hydrolytic conditions. Although fluorescence could be detected in the crude hydrolysates from the browned polypeptides, there appeared to be substantial quenching by UV-absorbing by-products.

Chromatography on arenesulfonic acid-type cation exchange resin proved to be unsuitable for separation of the fluorescent material; its failure to elute cleanly from this resin suggested that it was hydrophobic and/or weakly basic. Organic solvent extraction proved much more effective; thus, after mild alkalinization of the aqueous hydrolysates with ammonia or triethylamine, much of the fluorescence could be extracted into chloroform, while most of the brown color remained in the aqueous phase. By column chromatography of the chloroform extract on silica gel, it was possible to purify a single major fluorescent compound; this material has an Rf of 0.50 on silica gel TLC using ether-dichloromethane (1:4) as solvent.

Figure 2A:
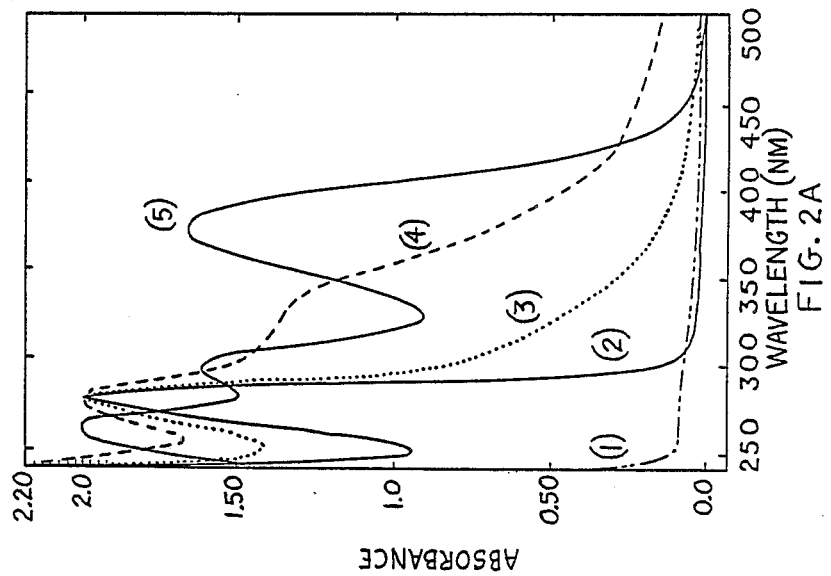

The fluorescent excitation spectra of BPL and BBSA and of the purified chromophore derived respectively from BPL and BBSA, are compared in FIG. 2B. The qualitative identity of these spectra is evident. The absorbances in the UV spectrum of the isolated chromophore (FIG. 2A, Curve 5), clearly correlate well with the fluorescence excitation maxima. These data suggest that the isolated material incorporates a principal Maillard-derived chromophoric center which has survived hydrolytic cleavage from the browned polypeptides without significant loss of chemical integrity.

Because the preliminary spectroscopic and chromatographic evidence indicated that the isolated chromophores from BPL and BBSA were identical, the more readily available BPL-derived material was principally used for the structure determination studies which follow; subsequent analysis of the BBSA derived chromophore under like conditions served to prove its identity with BPL-derived and chemically synthesized material.

EXAMPLE III

A. Spectrographic Analyses of the Fluorescent Isolate—Material and Methods

The isolated compounds were analyzed by thin layer chromatography on silica gel G using the solvent system ether-methylene chloride (1:4). The spots were visualized by ultraviolet light. HPLC analyses were carried out on prepacked silica gel columns (Porasil ®, 4 mm×300 mm, Waters Assoc., Milford, MA), with heptane-acetonitrile (3:2) as the mobile phase at a rate of 1 ml/min using a Hewlett Packard 1084B liquid chromatograph equipped with a variable wavelength detector. Absorption and fluorescent spectra were taken on a Hewlett Packard 8450A diode array spectrophotometer, and on a Perkin-Elmer 204 spectrofluorimeter, respectively. Absorption spectra were taken at a concentration of 1 mg/ml in 0.05M sodium phosphate buffer, pH 7.4. Fluorescence spectra were taken at 0.1 mg/ml in the same buffer. Acid hydrolysates were analyzed by ion-exchange TLC on FIXION ® chromatosheets (Chromatronix Inc. Mtn. View, CA), as described previously, Pongor, S., Kramer, J. and Ungar E. (1980) J. High. Res. Chrom. 3, pp. 93–94, using furosine and pyridosine standards.

$^1$H-NMR spectra were taken on a Nicolet NTC-300 (wide bore) spectrometer operated at 300 MHz in the Fourier transform mode. Samples were dissolved in CDCl$_3$. Chemical shifts of the compounds are given in ppm downfield from trimethylsilane.

B. Mass Spectrometry

A DuPont 21-492 double focusing magnetic deflection mass spectrometer modified for optional chemical ionization operation, equipped with a Varian 1400 gas chromatograph and coupled to a VG 2035 data system (VG Datasystems, Altringham, U.K.) was used. For low resolution (R=100) measurements, a combined electron impact/chemical ionization ion source was used, with a probe temperature of 180° C. Samples were introduced on ceramic probe tips; see, Bencsath, F. A. and Field, F. H. (1981) Abstracts, 29th Annual Conference on Mass Spectrometry and Allied Topics, Minneapolis, MN, May 24–29, 1981; American Society for Mass Spectrometry, East Lansing, MI; p. 587 or form a gas chromatograph column (1% SE-30, six feet long: temperature: 100° C. at sample injection, held three minutes and programmed to increase 10° C./min up to 250° C.).

For chemical ionization experiments isobutane was used as the reactant gas. Its pressure in the ion source was about 0.3 torr. For high resolution measurements (R=5,000) a dedicated electron impact source was used and samples were introduced in glass capillary probe cups. Twenty to twenty-five scans from three runs were averaged for the calculation of the elemental composition.

The electron impact mass spectrum of the chromophore isolate showed a relatively simple pattern dominated by three abundant ions m/z 228 (100%), 181 (33%), and 95 (88%). The isobutane chemical ionization mass spectrum consisted essentially of a single ion at m/z 229, corresponding to a molecular weight of 228 for the parent species. The elemental composition of the major ions was determined by averaged high resolution electron impact mass spectroscopy, the results of which are presented below in Table I.

TABLE I

HIGH RESOLUTION ELECTRON IMPACT MASS SPECTROMETRY OF FFI*

| Observed Mass | (m/z) | Computed Mass (m/z) | ΔM (millimass units) | Composition | Identity |
|---|---|---|---|---|---|
| 228.0 1 ± 0.0020 | (25) | 228.0534 | 1.4 | $C_{12}H_8N_3O_2$ | Molecular ion (M+.) |
| 160.0223 ± 0.0022 | (23) | 160.0272 | 5.0 | $C_8H_4N_2O_2$ | M+.- furan |
| 95.0140 ± 0.0018 | (25) | 95.0133 | −0.7 | $C_5H_3O_3$ | Furoyl ion |

*Observed data are given as mean ± standard error of the mean (number of determinations).

The molecular ion was found to have the formula $C_{12}H_8N_2O_3$. The formula of the m/z 95 fragment is that of the furoyl cation. The other major fragment, m/z 160, corresponds to the loss of the elements of neutral furan from the parent ion. This fragmentation pattern is consistent with a structure in which a 2-furoyl group and a group of formula $C_7H_5N_2O$ are linked together through a carbonyl group.

C. Chemical Derivatization for Mass Spectrometry

Derivatizations of FFI were carried out in 1 ml conical septum vials using 50 μg of BPL-derived FFI as a starting material. Methoxime formation was carried out by adding 100 μl of methoxyamine hydrochloride (Sigma, St. Louis, MO) as a 10% solution in pyridine, and incubating the solution at 80° C. for one hour. Blau, K. and King, G. S. (1977) *Handbook of Derivatives for Chromatography*, Heden; London, Bellmawr, N.J., pp. 243–244. Sodium borohydride reduction was carried out by adding 0.5 mg of solid NaBH$_4$ (Sigma, St. Louis, MO) to 100 μl of aqueous suspension of FFI. Ibid. pp. 332–333. After 20 minutes at room temperature the excess reagent was neutralized with a drop of glacial acetic acid. The solution was rendered alkaline with excess ammonium hydroxide, evaporated to dryness, and the reduced derivative was extracted from the residue with CH$_2$Cl$_2$. Monomethylation was carried out with 100 μl dimethylformamide dimethylacetal (Eastman Kodak, Rochester, NY) at 60° C. for two hours. Ibid. pp. 215–216. A portion of the monomethylated derivative was evaporated to dryness and treated with 100 μl of methyl iodide at 37° C. overnight to give a dimethylated derivative.

The chromophore material was found to form a monomethoxime derivative on reaction with methoxyamine, and underwent reduction with sodium borohydride with uptake of two hydrogens to yield a colorless derivative. Both derivatives have mass spectral fragmentation patterns markedly different from the parent compound. This behavior is consistent with the presence of a conjugated non-carboxylic carbonyl group. The results of this spectral analysis are set forth in Table II below.

TABLE II
MAIN IONS PRESENT IN ELECTRON IMPACT MASS SPECTRA OF FFI AND ITS CHEMICAL DERIVATIVES

| Compound | Main Ions (m/z) | Identity |
|---|---|---|
| FFI (underivatized) | 228 | M+. |
|  | 160 | M+. - C$_4$H$_4$O (loss of furan) |
|  | 95 | C$_5$H$_2$O$_2$ (furoyl cation) |
| FFI + methoxyamine | 257 | M+. for FFI methoxine |
| FFI + NaBH$_4$ | 230 | M+. for FFI + 2H |
|  | 212 | M+. - H$_2$O |
| FFI = dimethylformamide dimethyl acetal | 242 | M+. for monomethyl FFI - H |
| Monomethyl FFI + MeI | 257[1] | (M + 1) +. for dimethyl FFI |

[1] Obtained by fission fragment ionization mass spectrometry

Methylation studies demonstrated the presence of two nucleophilic sites which are differently susceptible to alkylation. Alkylation with dimethylformamide dimethyl acetal yields a neutral derivative in which one hydrogen has been replaced by methyl. Further methylation of this derivative with methyl iodide afforded a dimethyl derivative with chromatographic and mass spectroscopic properties of a quaternary methiodide salt. As shown in Table II, the molecular ion of the dimethyl derivative could only be detected under fission fragment ionization conditions, and not by electron impact or chemical ionization techniques.

D. $^1$H-NMR Spectrum of the Isolated Chromophore

FIG. 3 shows the $^1$H-NMR spectrum of the chromophore material from BPL. Double irradiation experiments demonstrated that resonances a, c, and d comprise a group of three mutually coupled protons, and that resonances b, f, and g comprise another similar but distinct group. Although one resonance in each group was anomalously broadened, there was sufficient structure in the other resonances to allow the estimation of the three coupling constants for each group. The H-H coupling constants are set forth in Table III, below.

TABLE III
H—H COUPLING CONSTANTS OF FFI FURAN RINGS

| Coupling Type | Observed Couplings Hz Furanyl Ring | Furoyl Ring | Typical Range, Hz* |
|---|---|---|---|
| furan H2–H3 | $J_{ac}$ = 3.4 | $J_{bg}$ = 3.6 | 3.1–3.8 |
| furan H3–H4 | $J_{ad}$ = 1.8 | $J_{bf}$ = 1.6 | 1.3–2.0 |
| furan H2–H4 | $H_{cd}$ = 0.7 | $J_{fg}$ = 0.5 | 0–1 |

In Table III, it may be seen that these constants fall well within the normal range observed for coupling constants in 2-substituted furan rings. Thus it appeared that, in addition to the furoyl group indicated by the mass spectral data, another chemically distinct 2-substituted furan ring was present. Subtracting a furoyl group and a furanyl group from the molecular formula leaves the elements of a disubstituted imidazole moiety.

The presence of an imidazole ring would account for the presence of two differentially nucleophilic centers; the tautomerism of the NH proton between two non-equivalent imidazole nitrogens, with a rate similar to the proton relaxation times, would explain the broadening of the 3-position hydrogen resonances in the furan rings. These factors together with mechanistic consideration for the formation of the chromophore led to the assignment of the structure as a 2-(2-furoyl)-4(5)-(2-furanyl)-1H-imidazole (FFI), the two tautomeric structures of which are shown in FIG. 4. The fact that the signal for H$_e$ on the imidazole ring is not broadened by the tautomerism may be due to fortuitous similarity of its chemical shifts in the two tautomers, or to effects on its relaxation time by the adjacent nitrogen quadrupole.

EXAMPLE IV

Identity of the Isolated Chromophore with Synthetic FFI

As a final confirmation of the assigned structure, FFI was prepared by an independent chemical method for comparison with polypeptide-derived material. A search of the literature failed to reveal any previous report on 2-(2-furoyl)-4(5)-(2-furanyl)1H-imidazole. However, a number of diphenyl analogs such as 2-benzoyl-4(5)-phenyl-1H-imidazole have been described. Schubert, W., Hellwig, A. and Bleichert, J. L. (1964) J. Prakt, Chem. 24, 125–131. These are most readily prepared by the reaction of phenylglyoxal derivatives with ammonia.

A solution of 2-furylglyoxal hydrate (710 mg) in a mixture of 10 ml ethanol and 3 ml of water was treated dropwise with 2 ml concentrated aqueous NH$_3$. After 80 minutes the brown solution was partitioned between H$_2$O and diethyl ether-dichloromethane (1:1). The organic layer was washed twice with water, dried with Na$_2$SO$_4$ and filtered. The filtrate was concentrated and the residue chromatographed on silica gel with ether-CH$_2$Cl$_2$ (6:94) as eluant. Fractions containing material which co-eluted on TLC with FFI from glycosylation experiments were pooled and concentrated, and the residue was recrystallized from ether.

On conducting an analogous reaction of furylglyoxal with ammonia in aqueous ethanol, a modest yield of FFI was isolated which was identical in all respects with the glycosylation derived materials. Accordingly, pure FFI (82 mg, 12%) was obtained as golden-yellow crystals with a brownish sheen: melting pt. 176°–177° C.; analysis: calculated for C$_{12}$H$_8$N$_2$O$_3$: C, 63.2%; H, 3.5%; N, 12.3%; found: C, 63.1%; H, 3.6%; N, 12.2%. The spectroscropic and chromatographic properties of this material were identical with those of the FFI samples derived from BPL and from BBSA. This is illustrated in FIG. 5, in which the electron impact mass spectra of synthetic FFI, BPL-derived FFI, and BBSA-derived FFI are compared.

As discussed briefly earlier herein, the fluorescence properties of FFI are remarkably similar to those of the non-dialyzable pigments bound to albumin and to polylysine which have undergone extensive non-enzymatic browning with glucose. This similarity implies that there is a close analogy between the structure of FFI and that of the chromophoric centers present in the fluorescent pigments. During subsequent acid hydrolysis, $\epsilon$-lysyl residues could cleave from the imidazole nitrogens via internal nucleophilic attack of their released $\alpha$-amino groups at the $\epsilon$-positions, forming FFI-like materials and pipecolic acid.

As described above, the structure FFI was deduced from mass spectroscopy, $^1$H-NMR spectroscopy, and chemical derivatization studies on the polypeptide-derived material. This tentative structure assignment was confirmed by comparison with FFI prepared from furylglyoxal and ammonia in a synthetic route used previously for the synthesis of a number of other diaryl 2-acyl imidazoles.

Like all unsymmetrically substituted imidazoles, FFI actually represents an equilibrium mixture of two interconverting tautomeric structures as illustrated in FIG. 4. For this reason, the NMR spectrum of FFI is very sensitive to traces of acid. In freshly prepared solutions of recrystallized synthetic FFI in CDCl$_3$, the exchange of the NH proton can be sufficiently slow that the broadened peaks in FIG. 3 resolve into separate broad peaks for each tautomer; conversely, addition of one equivalent of trifluoroacetic acid to the NMR solution to completely protonate both nitrogens leads to sharpening of the previously broad carbon-bound proton resonances, along with changes in chemical shifts (spectra not shown).

There are a number of different sequences in which two glucose molecules and two lysine $\epsilon$-amino goups could interact to form a tetrasubstituted imidazole system. Three of these possibilities are illustrated in FIG. 6.

In Route A, a lysine attacks the keto group of an $\epsilon$-fructosyllysine residue, followed by cyclization with a second glucose molecule. In Route B, two fructosyllysines interact with enolization and cyclization. In Route C, a difructosyllysine reacts with a second lysine followed by cyclization. The possibility of Route C is suggested by a previous observation of a product of the incubation of glucose with valine, which had two attached sugar residues. Koenig, R. J., Blobstein, S. H. and Cerami, A. (1977) J. Biol. Chem. 252, pp. 2992-2997. Both Routes A and C, in which fructosyllsine species interact with another amino group, might explain the attachment of proteins to other proteins that have previously undergone nonenzymatic browning. Brownlee, M., Pongor, S. and Cerami, A. (1983) J. Exp. Med. 158, pp. 1739-1744.

Cyclization to a tetrasubstituted dihydroimidazole (i.e., imidazoline) structure, and its subsequent autoxidation to a quaternary imidazolium species, would appear to be crucial steps in the formation of FFI. The dihydroimidazole imtermediate would be a highly electron-rich center, and its autoxidation under conditions of physiological oxygen tension in low-turnover proteins is not difficult to envision. At present it is difficult to assess the extent or rate at which subsequent dehydrations would occur in vivo to form one or both of the furan rings observed in FFI; such dehydrations could be facilitated in instances where the crosslinking of proteins via imidazole formation results in the creation of a hydrophobic microenvironment around the glucose-derived polyhydroxylic side chains.

The identification of FFI as a specific product that is characteristic of the late stage Maillard reaction provides a starting point from which further systematic studies of this process can proceed, with the aim of identifying other crosslinking and chromogenic moieties formed during the reaction. In the past, the only methods that have been available for measuring the presence of Maillard products in biological macromolecules were direct spectroscopic and fluorescence techniques using heterogeneous material. Monnier, V. M. and Cerami, A. (1981) Science, 211, pp. 491-493. The measurement of a specific compound, FFI, derived from specific Maillard intermediates, may provide a new approach to quantitating the primary sites of crosslinking formed during aging of proteins and nucleic acids. Monnier, V. M. and Cerami, A. (1981) Science, 211, pp. 491-493 and Bucala, R., Model, P. and Cerami, A. (1983) Proc. Natl. Acad. Sci. (in press). In the clinical study of aging and of diabetes, measurement of FFI may allow assessment of the time-averaged exposure of long-lived structural tissues to glucose over extended periods (months to years), analogous to the current utility of HbA$_{1c}$ levels in estimating glucose exposure over 3-4 week periods. In addition, the quantitation of FFI formed in vivo in conjunction with concurrent clinical observations should provide new insight into specific roles of Maillard products in the complications of aging and diabetes.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A test kit for the detection of advanced glycosylation end products of polypeptides, comprising:
   a. a predetermined amount of the labeled chromophore 2-(2-furoyl)-4(5)-(2-furanyl)-1H-imidazole or the binding partner specific thereto;
   b. other reagents; and
   c. directions for use of said kit.

2. A test kit to be used for the detection and/or determination of a component selected from the group consisting of 2-(2-furoyl)-4(5)-2(2-furanyl)-1H-imidazole, and the specific binding partners thereto, according to a predetermined protocol, comprising:
   a. a labeled component which has been obtained by coupling said component to a detectable label;
   b. one or more additional immunochemical reagents of which at least one reagent is a ligand or an immobilized ligand, which ligand is selected from the group consisting of:
      i. a ligand capable of binding with the labeled component a.;
      ii. a ligand capable of binding with a binding partner of the labeled component a.;
      iii. a ligand capable of binding with at least one of the component(s) to be determined; and iv. a ligand capable of binding with at least one of the binding partners of at least one of the component(s) to be determined; and c. directions for the performance of a protocol for the detection and/or determination of one or more components of an immunochemical reaction between said 2-(2-furoyl)-4(5)-(2-furanyl)-1H-imidazole and a specific binding partner thereto.

3. An indicator composition for use in an assay procedure for the detection of advanced glycosylation end products in polypeptide samples, said composition comprising the fluorescent chromophore 2-(2-furoyl)-4(5)-(2-furanyl)-1H-imidazole.

4. The indicator of claim 3 having associated therewith a detectible label.

5. The indicator of claim 4 wherein the label is an enzyme.

6. The indicator of claim 5 wherein the label is selected from peroxidase, β-glucuronidase, β-D-glucosidase, β-D-galactosidase, urease, glucose oxidase plus peroxidase, galactose oxidase plus peroxidase, and acid phosphatase.

7. The indicator of claim 4 wherein said label is a radioactive element.

8. The indicator of claim 7 wherein said radioactive element is selected from the group consisting of $^{14}C$, $^{125}I$, $^{131}I$, $^{35}S$ and $^{3}H$.

9. The indicator of claim 4 wherein said label is a chemical which fluoresces when exposed to ultraviolet light.

10. The indicator of claim 9 wherein said chemical is selected from fluorescein, rhodamine, and auramine.

11. A method for measuring the degree of aging of a protein sample in which nonenzymatic glycosylation is suspected to be occuring, comprising measuring the presence and amount of the fluorescent chromophore 2-(2-furoyl)-4(5)-(2-furanyl)-1H-imidazole in said protein sample and comparing the results of said measurement with the results of measurements of protein samples having a known degree of said advanced glycosylation.

* * * * *